US00PP20934P2

(12) United States Plant Patent
Giesen

(10) Patent No.: US PP20,934 P2
(45) Date of Patent: Apr. 13, 2010

(54) *DIASCIA* PLANT NAMED 'DALA ABLOS'

(50) Latin Name: *Diascia barberae*
Varietal Denomination: Dala Ablos

(75) Inventor: Eric Giesen, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 12/313,710

(22) Filed: Nov. 24, 2008

(51) Int. Cl.
*A01H 5/00* (2006.01)

(52) U.S. Cl. ..... Plt./425

(58) Field of Classification Search ..... Plt./263, Plt./425

See application file for complete search history.

*Primary Examiner*—Susan B McCormick Ewoldt
(74) *Attorney, Agent, or Firm*—S. Matthew Edwards

(57) ABSTRACT

A new *Diascia* plant named 'Dala Ablos' particularly distinguished by large blush white flowers with pink markings, deep green foliage, rounded leaves, moderately vigorous growth, and a densely branched, mounding to semi-trailing, medium sized plant habit is disclosed.

1 Drawing Sheet

Latin name of the genus and species of the plant claimed: *Diascia barberae.*

Varietal denomination: 'Dala Ablos'.

BACKGROUND OF THE NEW PLANT

The present invention comprises a new *Diascia,* botanically known as *Diascia barberae,* and hereinafter referred to by the variety name 'Dala Ablos.'

'Dala Ablos' is a product of a planned breeding program. The new cultivar' originated from a hybridization made in June 2005 in a controlled breeding program in Andijk, Netherlands.

The female parent was an unpatented, proprietary *Diascia* plant designated 'DSZ-39-8,' having a different salmon flower color and larger and less deep green leaves than 'Dala Ablos.'

The male parent of 'Dala Ablos' was an unpatented, proprietary *Diascia* plant designated 'DSZ-41-3,' having a deeper, light rose, flower color, larger flowers, and longer stems than 'Dala Ablos.'

The seeds were sown in October 2005 and 'Dala Ablos' was selected as one flowering plant within the progeny of the stated cross in January 2006 in a controlled environment in Andijk, Netherlands.

The first act of asexual reproduction of 'Dala Ablos' was accomplished when vegetative cuttings were taken from the initial selection in the spring of 2006 in a controlled environment in Andijk, Netherlands.

Horticultural examination of plants grown from cuttings of the plant initiated in the spring of 2006 in Andijk, Netherlands, and in Hillscheid, Germany, and continuing thereafter, has demonstrated that the combination of characteristics as herein disclosed for 'Dala Ablos' are firmly fixed and are retained through successive generations of asexual reproduction.

'Dala Ablos' has not been observed under all possible environmental conditions. The phenotype may vary significantly with variations in environment such as temperature, light intensity and day length.

A Plant Breeder's Right for this cultivar was applied for in the European Union on Jul. 21, 2008. 'Dala Ablos' has not been made publicly available more than one year prior to the filing of this application.

DESCRIPTION OF DRAWING

This new *Diascia* plant is illustrated by the accompanying photograph which shows blooms, buds, and foliage of the plant in full color. The colors shown are as true as can be reasonably obtained by conventional photographic procedures. The photograph, taken in late May 2008, is of a 25 cm diameter basket holding three 15 week old plants grown in a greenhouse during a spring trial setting. The inset shows a close view of a single flower.

DETAILED BOTANICAL DESCRIPTION

The measurements were taken in Hillscheid, Germany, mainly on Apr. 5, 2008 using 8 week old plants that were growing on benches in a greenhouse. Culture of these plants had started in early February with planting rooted cuttings into 12 cm pots. Additional observations were made during the summer of 2008.

Color chart used: The Royal Horticultural Society Colour Chart (R.H.S.), 2001.

BRIEF SUMMARY OF INVENTION

The following observations, measurements, and comparisons describe plants grown indoors and outdoors in Andijk, Netherlands, and in Hillscheid, Germany. The following traits have been repeatedly observed and are determined to be basic characteristics of the new variety. The combination of these characteristics distinguishes this *Diascia* as a new and distinct variety:

1. Large, nearly white flowers with pink markings
2. Deep green foliage, medium sized leaves
3. Good branching characteristics, moderately tight structure
4. Medium sized, bushy, mounded and somewhat trailing plant habit
5. Suitable for container planting and hanging baskets

COMPARISON WITH COMMERCIAL CULTIVARS

TABLE 1

| | 'Dala Ablos' | 'Diasupa' (U.S. Plant Pat. No. 18,837) | 'Dala Litpink' (U.S. Plant Pat. No. 17,215) |
|---|---|---|---|
| Main flower color (RHS) | 69C-69 D | 69C (69B margins) | Deeper pink, 65B |
| Flower markings (RHS) | 68B (ring) N66C (stamen) 69D (spur) | N66C-D (ring) 71C-D (stamen) 72C (spur) | N57C, relatively weak N66C (stamen) 68B (spur) |
| Flower size | 2.4-2.6 cm | 2.2-2.4 cm | 2.4-2.6 cm |
| Foliage color | Partly deeper than 137A | 137A to 137B | 137A |
| Leaf shape | Rounded | More pointed | Rounded |
| Stem length | Up to 20 cm | Up to 30 cm (distinctly longer in greenhouse, less obviously different later outdoors) | Up to 20 cm |

'Dala Ablos' differs from the commercial cultivar 'Flying Colors Appleblossom' (U.S. Plant Pat. No. 18,837, 'Diasupa') in that 'Dala Ablos' has a close overall flower color, but less deep pink markings, and lighter, nearly white spurs, slightly larger flowers, but somewhat smaller plant habit.

'Dala Ablos' differs from the commercial variety 'Darla Light Pink' ('Dala Litpink,' U.S. Plant Pat. No. 17,215) mainly by its flower color; it has roughly same flower and plant size.

Plant:

*Plant habit.*—Bushy, rounded, initially semi-upright, later mounding to semi-trailing, medium in size.

*Height.*—12 cm (from top of soil) for 8 week old plants.

*Width (diameter).*—Approximately 30 cm.

*Spread (including flowers).*—17–21 cm, from the base of the main stem to the tips of the branches.

*Time to produce a finished flowering plant.*—About 8 weeks for a flowering plant in a 12 cm pot.

*Time to initiate and develop roots.*—About 14 days, respective 21 days for a saleable, pinched young plant.

*Outdoor plant performance.*—Free-flowering through the summer months; has some heat tolerance; use in mixed container planting or hanging-baskets.

Stem:

*Characteristics.*—Side branches are developed at almost every node.

*Stem length.*—Approximately 16–19 cm including the inflorescence.

*Diameter.*—0.3 cm in the middle part.

*Internode length.*—2.0–3.0 cm.

*Color.*—RHS 153B, grass-green, no anthocyanin.

*Texture.*—Appears smooth and glabrous, but has sparse short hair.

Foliage:

*Arrangement.*—Single and opposite, decussate at non-flowering stems.

*Shape.*—Cordate.

*Apex.*—Obtuse to rounded.

*Base.*—Cordate.

*Margin.*—Weakly crenate.

*Leaf length.*—1.8–2.3 cm.

*Leaf width.*—2.0–2.2 cm.

*Immature leaf, color upper surface.*—RHS 137C.

*Immature leaf, color lower surface.*—RHS 138B.

*Mature color upper surface.*—Deep green, RHS 137A or even intermediate between 137A and 139A.

*Mature color lower surface.*—RHS 138B.

*Venation type.*—Pinnate.

*Venation color.*—RHS 144B.

*Texture.*—Appears smooth and glabrous on both sides.

Petiole:

*Length.*—0.1–0.2 cm.

*Petiole width.*—0.2 cm.

*Petiole color.*—RHS 144A.

Flower bud:

*Shape.*—Initially a somewhat flattened half-globe/semi-sphere.

*Width.*—0.7 cm.

*Length.*—0.4 cm.

*Color (at tight bud).*—Pale pink, RHS 56D.

Inflorescence:

*Type.*—Terminal raceme with flowers in an alternate arrangement at a distance of 0.5–1.0 cm.

*Blooming habit.*—Continuous through the summer months.

*Quantity of inflorescences per plant.*—From 30 to 50.

*Number of flowers per inflorescence.*—Most often 6–7 open flowers, additional buds.

*Lastingness of individual blooms on the plant.*—3–4 days.

*Fragrance.*—None.

*Inflorescence length.*—Most often 10–13 cm.

*Inflorescence diameter.*—4.3–4.8 cm.

Peduncle:

*Color.*—RHS 143A.

*Length.*—9–12 cm.

*Diameter.*—0.2 cm.

*Texture.*—Pubescent.

Flower:

*Corolla type and shape.*—Single-type, zygomorphic; salver-shape, 5 petals fused at the base, the two small upper petals mainly fused, two lateral lobes and a broad lower lobe; two short spurs emerge at the underside, formed by the lower ends of lateral and lower petals.

*Length.*—2.4–2.6 cm.

*Width.*—2.3–2.5 cm.

*Depth.*—0.4 cm.

*Color upper surface.*—Nearly white, palest pink, RHS 69D.

*Color lower surface.*—Pale pink, RHS 69A or 69B to white, RHS N155B.

*Markings in the center.*—Pink, RHS 62B or lighter; upper petals have a patch of RHS 9B (yellow) at the base.

Petals (lobes):

*Apex.*—Rounded.

*Base.*—Fused.

*Margin.*—Entire.

*Texture.*—Smooth, glabrous on both sides.

*Upper lobes, length (from the corolla opening).*—0.6–0.7 cm.

*Upper lobes, width (joint).*—1.2 cm.

*Lateral lobes, length (from the corolla opening).*—0.5–0.7 cm.

*Lateral lobes, width.*—0.9 cm.
*Lower lobe, length* (*from the corolla opening*).—1.1 cm.
*Lower lobe, width.*—1.6 cm.

Spurs:
*Shape and aspect.*—2, short, horn-shaped and downwards directed.
*Spur length.*—0.7–0.9 cm.
*Spur diameter.*—0.3 cm at upper end.
*Spur color.*—Mainly RHS 69D, RHS 70B at the tip.

Calyx: 5 sepals, slanting downwards.
*Sepal color.*—RHS 137D.
*Length.*—0.2–0.3 cm.
*Width.*—0.15 cm.
*Shape.*—Deltoid.
*Apex.*—Acute.
*Base.*—Fused.
*Texture, upper surface.*—Glabrous.
*Texture, lower surface.*—Covered with glandular hair.

Pedicels:
*Color.*—RHS 144B at flower to RHS 137D at lower end.
*Length.*—1.5–2.0 cm.
*Diameter.*—0.1 cm.
*Texture.*—Dense hair, hirsute.

Reproductive organs:

Stamens:
*Quantity and arrangement.*—4; coherent, arching towards and somewhat twisting around the pistil.
*Filament, color.*—RHS 70B to 70C (dull purple-pink).
*Length.*—0.3–0.4 cm.
*Diameter.*—0.1 cm.
*Anther color.*—RHS 11A, yellow.
*Pollen amount.*—Abundant.
*Pollen color.*—RHS 12B.

Pistil:
*Quantity per flower.*—One.
*Length.*—0.3–0.4 cm.
*Stigma color.*—RHS 154A.
*Style color.*—RHS 145C.

Fruit and seed set: Has not been observed.

Disease/pest resistance: Typical for the species, no special observations made.

What is claimed is:

1. A new and distinct variety of *Diascia* plant named 'Dala Ablos,' substantially as illustrated and described herein.

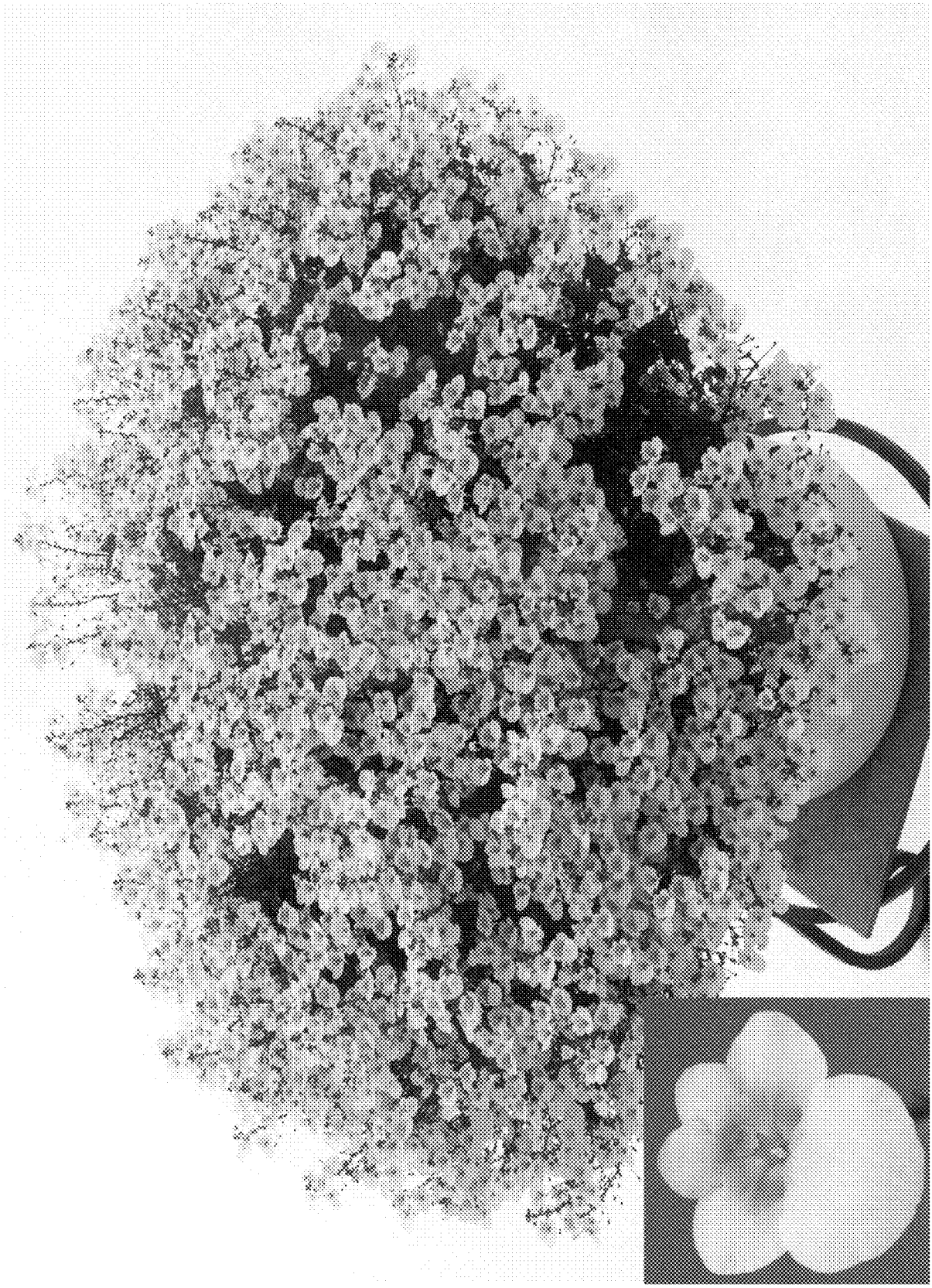

* * * * *